(12) United States Patent
Zhang et al.

(10) Patent No.: US 7,890,188 B2
(45) Date of Patent: *Feb. 15, 2011

(54) IMPLANTABLE LEAD FOR SEPTAL PLACEMENT OF ELECTRODE WITH FIXATION MECHANISM IN THE PULMONARY ARTERY

(75) Inventors: Yongxing Zhang, Little Canada, MN (US); James O. Gilkerson, Stillwater, MN (US); Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1314 days.

This patent is subject to a terminal disclaimer.

(21) Appl. No.: 10/325,658

(22) Filed: Dec. 19, 2002

(65) Prior Publication Data
US 2004/0122497 A1    Jun. 24, 2004

(51) Int. Cl.
*A61N 1/05* (2006.01)
(52) U.S. Cl. .......................... 607/122; 607/1; 607/119; 607/123; 607/126; 607/127; 607/128; 600/375
(58) Field of Classification Search ............... 606/126; 607/125–128, 122–123, 119, 1; 600/375
See application file for complete search history.

(56) References Cited

U.S. PATENT DOCUMENTS

| | | | |
|---|---|---|---|
| 3,995,623 A | 12/1976 | Blake et al. | |
| 4,402,328 A | 9/1983 | Doring | |
| 4,488,561 A | 12/1984 | Doring | 128/786 |
| 4,595,009 A | 6/1986 | Leinders | |
| 4,627,439 A | 12/1986 | Harris | |
| 4,641,656 A | 2/1987 | Smits | |
| 4,643,201 A | 2/1987 | Stokes | 128/786 |
| 4,759,378 A | 7/1988 | Swendson et al. | |
| 4,986,270 A | 1/1991 | Cohen | 128/419 |
| 5,000,190 A | 3/1991 | Petre | |
| 5,029,585 A | 7/1991 | Lieber et al. | |
| 5,144,960 A * | 9/1992 | Mehra et al. | 607/125 |

(Continued)

OTHER PUBLICATIONS

Barin, E. S., et al., "The right ventricular outflow tract as an alternative permanent pacing site: long-term follow-up", *Pacing and Clinical Electrophysiology*, 14(I), (1991),3-6.

(Continued)

*Primary Examiner*—Carl H Layno
*Assistant Examiner*—Deborah Malamud
(74) *Attorney, Agent, or Firm*—Faegre & Benson LLP

(57) ABSTRACT

A lead body includes an electrode coupled to an intermediate portion of the lead body. A distal end of the lead includes a pre-formed, biased shape adapted to passively fixate the distal end of the lead within a pulmonary artery with the electrode positioned in the right ventricle or ventricular outflow tract. The lead body can include a preformed J-shape, with the electrode coupled to the intermediate portion of the lead body and located distally from a bottom of the pre-formed J-shape. The lead body can include a section of the intermediate portion of the lead body being less stiff than adjacent sections of the lead body with the electrode coupled to the intermediate portion of the lead body and located distally from the less stiff section.

17 Claims, 4 Drawing Sheets

U.S. PATENT DOCUMENTS

| | | | | |
|---|---|---|---|---|
| 5,314,462 | A | * | 5/1994 | Heil et al. .................... 607/128 |
| 5,387,233 | A | * | 2/1995 | Alferness et al. ............. 607/126 |
| 5,403,351 | A | | 4/1995 | Saksena .......................... 607/4 |
| 5,405,374 | A | | 4/1995 | Stein ........................... 607/122 |
| 5,411,527 | A | | 5/1995 | Alt ................................. 607/5 |
| 5,423,772 | A | * | 6/1995 | Lurie et al. .................. 604/525 |
| 5,423,806 | A | | 6/1995 | Dale et al. |
| 5,423,865 | A | * | 6/1995 | Bowald et al. .................. 607/5 |
| 5,433,729 | A | * | 7/1995 | Adams et al. ................... 607/5 |
| 5,433,742 | A | | 7/1995 | Willis |
| 5,476,499 | A | | 12/1995 | Hirschberg |
| 5,571,159 | A | * | 11/1996 | Alt .............................. 607/122 |
| 5,609,621 | A | | 3/1997 | Bonner |
| 5,628,779 | A | | 5/1997 | Bornzin et al. |
| 5,643,338 | A | * | 7/1997 | Bornzin et al. .............. 607/123 |
| 5,697,965 | A | | 12/1997 | Griffin, III |
| 5,788,647 | A | | 8/1998 | Eggers ........................ 600/526 |
| 5,800,498 | A | | 9/1998 | Obino et al. |
| 5,861,023 | A | | 1/1999 | Vachon |
| 5,922,014 | A | * | 7/1999 | Warman et al. ............. 607/123 |
| 5,925,073 | A | | 7/1999 | Chastain et al. |
| 6,006,122 | A | * | 12/1999 | Smits .......................... 600/373 |
| 6,021,354 | A | | 2/2000 | Warman et al. |
| 6,070,104 | A | | 5/2000 | Hine et al. |
| 6,076,014 | A | | 6/2000 | Alt ................................. 607/4 |
| 6,093,982 | A | | 7/2000 | Kroll |
| 6,117,128 | A | * | 9/2000 | Gregory ......................... 606/7 |
| 6,122,553 | A | | 9/2000 | Ideker et al. |
| 6,132,390 | A | | 10/2000 | Cookston et al. |
| 6,216,027 | B1 | | 4/2001 | Willis et al. |
| 6,245,064 | B1 | | 6/2001 | Lesh et al. |
| 6,363,286 | B1 | | 3/2002 | Zhu et al. .................... 607/120 |
| 6,363,287 | B1 | | 3/2002 | Brabee et al. |
| 6,501,992 | B1 | | 12/2002 | Belden et al. |
| 6,532,378 | B2 | | 3/2003 | Saksena et al. |
| 6,718,211 | B2 | | 4/2004 | Smits |
| 6,741,893 | B2 | * | 5/2004 | Smits .......................... 607/122 |
| 6,760,619 | B1 | | 7/2004 | Helland et al. |
| 6,882,886 | B1 | | 4/2005 | Witte et al. |
| 7,392,094 | B2 | | 6/2008 | Zhang et al. |
| 7,555,351 | B2 | | 6/2009 | Zhang et al. |
| 2001/0031987 | A1 | | 10/2001 | Saksena et al. |
| 2002/0065544 | A1 | * | 5/2002 | Smits .......................... 607/122 |
| 2004/0122496 | A1 | | 6/2004 | Zhang et al. |
| 2004/0122497 | A1 | | 6/2004 | Zhang et al. |
| 2004/0122498 | A1 | | 6/2004 | Zhang et al. |
| 2004/0260374 | A1 | | 12/2004 | Zhang et al. |
| 2004/0260375 | A1 | | 12/2004 | Zhang et al. |
| 2005/0149155 | A1 | | 7/2005 | Scheiner et al. |
| 2005/0149156 | A1 | | 7/2005 | Libbus et al. |
| 2007/0299492 | A1 | | 12/2007 | Zhang et al. |
| 2008/0262586 | A1 | | 10/2008 | Zhang et al. |
| 2009/0264974 | A1 | | 10/2009 | Zhang et al. |

OTHER PUBLICATIONS

Belham, M , et al., "Pacing Different ventricular site with active and passive fixation leads: comparison of pacing energy requirements", *Pacing and Clinical Electrophysiology*, 21(II), (1999),977.

Buckingham, T. A., et al., "Right ventricular outflow tract pacing", *Pacing and Electrophysiology*, 20(5 Pt 1), (1997),1237-42.

Giudici, M. , et al., "Comparison of right ventricular outflow tract and apical lead permanent pacing on cardiac output", *American Journal of Cardiology*, 79(2), (1997),209-212.

Giudici, M. C., et al., "Right ventricular outflow tract pacing improves haemodynamics in patients with class III-IV heart failure and existing apical leads", *Pacing and Electrophysiology*, 21(II) Abstract 751, (1998),2 pgs.

Harris, Z I., et al., "Changes in left ventricular function and dimensions between apical and septal lead position with dual chamber pacing in normally functioning hearts", *Pacing and Clinical Electrophysiology*, 22(II) Abstract, (1999),751.

Harris, Z. I., et al., "Septal/right ventricular outflow tract (RVOT) lead placement", *Pacing and Electrophysiology*, 22(12), (1999),1854.

Hirschberg, J. , "A New Dual Chamber Single Lead System", *Pacing & Electrophysiology*, 17(11 Pt 2), (Nov. 1994),1870-1872.

Lubinski, A. , et al., "Implantation and follow-up of ICD leads implanted in the right ventricular outflow tract", *Pacing and Electrophysiology*, 23(11 Pt 2), (2000),1996-98.

Mera, F. , et al., "A comparison of ventricular function during high right ventricular septal and apical pacing after his-bundle ablation for refractory atrial fibrillation", *Pacing and Clinical Electrophysiology*, 22(8), (1999),1234-39.

Rosenqvist, M , et al., "The effect of ventricular activation on cardiac performance during pacing", *Pacing and Electrophysiology*, 19(9), (1996),1279-1286.

Schwaab, B , et al., "Influence of right ventricular stimulation site on left ventricular function in atrial synchronous ventricular pacing", *Journal of the American College of Cardiology*, 33(2), (1999),317-23.

Schwaab, B , et al., "Surface ECG guided right ventricular septal lead implantation for the reduction of paced QRS duration", *Pacing and Clinical Electrophysiology*, 22(II), (1999),806.

Staniewicz, J , et al., "Short versus long term results in right ventricular outflow tract pacing- prospective randomized study", *Pacing and Electrophysiology*, 21(II) Abstract 419, (1998),2 pgs.

Tang, A.S.L. , et al., "Nonthorocotomy implantation of cardioverter defribrillators; preliminary experience with a defribrillation lead paced at the right ventricular outflow tract", *Pacing and Electrophysiology*, 19(6), (1996),960-964.

Tantengco, M. V., et al., "Left ventricular dysfunction after long-term right ventricular apical pacing in the young", *American Journal of Cardiology*, 37(8), (Jun. 15, 2001),2093-100.

Victor, F. , et al., "Optimal right ventricular pacing site in chronically implanted patients", *Journal of the American College of Cardiology*, 33(2), (1999),311-6.

Vlay, S. C., et al., "Alternative locations for internal defibrillator electrodes", *Pacing and Clinical Electrophysiology*, 21(6), (1998),1309-12.

Wolfhard, U. F., et al., "Alternative lead positioning in the right ventricular outflow tract in transvenous implantation of ICDs", *Pacing and Electrophysiology*, 18(1Pt 2), (1995),179-81.

Zhang, Yongxing , "Delivery System and Method for Pulmonary Artery Leads", *U.S. Appl. No. 10/970,265, filed Oct. 20, 2004*, 21 pgs.

Giudici, M C., "Improvement in Cardiac Output with Right Ventricular Outflow Septal Pacing Compare to Apical Pacing is Independent of Pre-existing Conduction Disease", *Pacing and clinical electrophysiology : PACE*, 23(4), (2000),748.

Scherlag, B. J., et al., "Endovascular stimulation within the left pulmonary artery to induce slowing of heart rate and paroxysmal atrial fibrillation.", *Cardiovasc Research*, 54(2), (May 2002),470-475.

Tse, Hung-Fat , "Functional abnormalities in patients with permanent right ventricular pacing—The effect of sites of electrical stimulation", *Journal of the American College of Cardiology*, 40(8), (Oct. 16, 2002),1451-1458.

Advisory Action mailed Mar. 20, 2007 in U.S. Appl. No. 10/895,747, 3 pgs.

Advisory Action mailed Jul. 23, 2007 in U.S. Appl. No. 10/325,659, 3 pgs.

Amendment and Response mailed Oct. 18, 2006 in U.S. Appl. No. 10/895,747, 14 pgs.

Amendment and Response mailed Nov. 22, 2006 in U.S. Appl. No. 10/325,433, 17 pgs.

Amendment and Response mailed Dec. 9, 2005 in U.S. Appl. No. 10/325,659, 15 pgs.

Amendment and Response mailed Feb. 5, 2007 in U.S. Appl. No. 10/325,659, 13 pgs.

Amendment and Response mailed May 25, 2006 in U.S. Appl. No. 10/325,659, 14 pgs.

Amendment and Response to Final Office Action mailed Feb. 22, 2007 in U.S. Appl. No. 10/895,747, 18 pgs.

Final Office Action mailed Dec. 22, 2006 in U.S. Appl. No. 10/895,747, 9 pgs.
Final Office Action mailed May 3, 2007 in U.S. Appl. No. 10/325,659, 17 pgs.
Non Final Office Action mailed Jun. 1, 2007 in U.S. Appl. No. 10/325,433, 9 pgs.
Non Final Office Action mailed Jun. 12, 2007 in U.S. Appl. No. 10/895,748, 8 pgs.
Non-Final Office Action mailed Aug. 9, 2005 in U.S. Appl. No. 10/325,659, 16 pgs.
Non-Final Office Action mailed Jan. 25, 2006 in U.S. Appl. No. 10/325,659, 14 pgs.
Non-Final Office Action mailed Nov. 16, 2005 in U.S. Appl. No. 10/325,433, 14 pgs.
Non-Final Office Action mailed Jul. 18, 2006 in U.S. Appl. No. 10/895,747, 16 pgs.
Non-Final Office Action mailed Jul. 31, 2006 in U.S. Appl. No. 10/325,433, 15 pgs.
Non-Final Office Action mailed Jul. 5, 2007 in U.S. Appl. No. 10/895,747, 13 pgs.
Non-Final Office Action mailed Aug. 4, 2006 in U.S. Appl. No. 10/325,659, 14 pgs.
Request for Continued Examination mailed Apr. 23, 2007 in U.S. Appl. No. 10/895,747, 1 pg.
Response mailed May 16, 2006 in U.S. Appl. No. 10/325,433, 16 pgs.
Response to Final Office Action mailed Jul. 3, 2007 in U.S. Appl. No. 10/325,659, 15 pgs.
"U.S. Appl. No. 10/325,433 Non Final office action mailed Jun. 1, 2007", 9 pgs.
"U.S. Appl. No. 10/325,433, Response filed Sep. 4, 2007 to Non-Final Office Action mailed Jun. 1, 2007", 15 pgs.
"U.S. Appl. No. 10/895,747 Response filed Oct. 5, 2007 to Non-Final Office Action Mailed Jul. 5, 2007", 17 Pages.
"Final Office Action mailed Oct. 26, 2007 in U.S. Appl. No. 10/325,433", FOAR,10 pgs.
"U.S. Appl. No. 10/325,433 Notice of Allowance mailed Feb. 21, 2008.", 5 pgs.
"U.S. Appl. No. 10/895,747 Advisory Action mailed Mar. 18, 2008", 2 pgs.
"U.S. Appl. No. 10/325,433 Response filed Dec. 21, 2007 to Final Office Action mailed Oct. 26, 2007", 16 pages.
"U.S. Appl. No. 10/325,443 Response filed Jan. 28, 2008 to Final Office Action mailed Oct. 26, 2007 and Advisory Action mailed Jan. 15, 2008", 8 pages.
"U.S. Appl. No. 10/895,747 Response filed Feb. 19, 2008 to Final Office Action mailed Dec. 19, 2007", 18 pages.
"U.S. Appl. No. 10/895,747, Final Office Action mailed Dec. 19, 2007", 9 pgs.
"U.S. Appl. No. 10/325,433, Advisory Action mailed Jan. 5, 2008", 3 pgs.
"U.S. Appl. No. 10/325,433, Examiner Interview Summary mailed Feb. 21, 2008", 1 pg.

"U.S. Appl. No. 10/325,659, Appeal Brief filed Dec. 3, 2007", 26 pgs.
"U.S. Appl. No. 10/325,659, Examiner Interview Summary mailed Jan. 25, 2006", 1 pg.
"U.S. Appl. No. 10/325,659, Pre-Appeal Brief Request filed Oct. 3, 2007", 5 pgs.
"U.S. Appl. No. 10/895,747, Appeal Brief mailed Jul. 2, 2008", 19 pgs.
"U.S. Appl. No. 10/895,747, Pre Appeal Brief Request mailed Apr. 21, 2008", 5 pgs.
"U.S. Appl. No. 11/895,808, Response filed Apr. 24, 2009 to Restriction Requirement mailed Mar. 24, 2009", 8 pgs.
"U.S. Appl. No. 11/895,808, Restriction Requirement mailed Mar. 24, 2009", 13 pgs.
Libbus, Imad, "Lead for Stimulating the Baroreceptors in the Pulmonary Artery", U.S. Appl. No. 10/746,861, filed Dec. 24, 2003, 21 pages.
Scheiner, Avram, "Stimulation Lead for Stimulating the Baroreceptors in the Pulmonary Artery", U.S. Appl. No. 10/746,852, Filed Dec. 24, 2003, 25 pages.
U.S. Appl. No. 10/325,659, Non-Final Office Action mailed Jun. 1, 2007, 9 pages.
U.S. Appl. No. 10/325,659, Decision on Pre-Appeal Brief mailed Oct. 31, 2007, 2 pages.
U.S. Appl. No. 10/325,659, Examiner's Answer mailed Feb. 22, 2008, 25 pages.
U.S. Appl. No. 10/325,659, Appellants' Reply Brief filed Apr. 22, 2008, 5 pages.
U.S. Appl. No. 10/895,748, Non Final Office Action mailed Sep. 25, 2006, 9 pages.
U.S. Appl. No. 10/895,748, Response filed Dec. 22, 2006 to Non Final Office Action mailed Sep. 25, 2006, 13 pages.
U.S. Appl. No. 10/895,748, Final Office Action mailed Mar. 28, 2007, 9 pages.
U.S. Appl. No. 10/895,748, Response filed May 29, 2007 to Final Office Action mailed Mar. 28, 2007, 13 pages.
U.S. Appl. No. 10/895,748, Response filed Sep. 12, 2007 to Non-final Office Action Mailed Jun. 12, 2007, 12 pages.
U.S. Appl. No. 10/895,748, Final Office Action mailed Jan. 31, 2008, 9 pages.
U.S. Appl. No. 10/895,748, Response filed Mar. 31, 2008 to Final Office Action mailed Jan. 31, 2008, 12 pages.
U.S. Appl. No. 10/895,748, Non-final Office Action Mailed May 16, 2008, 10 pages.
U.S. Appl. No. 10/895,748, Response filed Aug. 15, 2008 to Non-final Office Action Mailed May 16, 2008, 13 pages.
U.S. Appl. No. 10/895,748, Final Office Action mailed Nov. 19, 2008, 9 pages.
U.S. Appl. No. 10/895,748, Response filed Jan. 21, 2009 to Final Office Action mailed Nov. 19, 2008, 8 pages.
U.S. Appl. No. 10/895,748, Notice of Allowance mailed Feb. 27, 2009, 6 pages.

* cited by examiner

IMPLANTABLE LEAD FOR SEPTAL PLACEMENT OF ELECTRODE WITH FIXATION MECHANISM IN THE PULMONARY ARTERY

FIELD OF THE INVENTION

This invention relates to the field of medical leads, and more specifically to an implantable lead.

BACKGROUND

Leads implanted in or about the heart have been used to reverse certain life threatening arrhythmia, or to stimulate contraction of the heart. Electrical energy is applied to the heart via an electrode to return the heart to normal rhythm. Leads are usually positioned in the ventricle or in the atrium through a subclavian vein, and the lead terminal pins are attached to a pacemaker which is implanted subcutaneously.

For example, one approach is to place the electrode against the ventricular septum above the apex. However, current leads require a lead placed with the electrode against the septum above the apex to be actively fixated. This may possibly result in trauma to the heart from cyclical heart motion, and lead to micro-dislodgement of the electrode, and relatively higher defibrillating and pacing thresholds. Moreover, other factors which can be improved include better electrode contact, and easier implanting and explanting of the leads.

SUMMARY

A lead body having an electrode coupled to an intermediate portion of the lead body. A distal end of the lead includes a pre-formed, biased shape adapted to passively fixate the distal end of the lead within a pulmonary artery with the electrode positioned at the ventricular septum or ventricular outflow tract.

Another aspect includes a lead body configured into a pre-formed J-shape. The lead includes an electrode coupled to an intermediate portion of the lead body and located distally from a bottom of the pre-formed J-shape. The lead is adapted to be placed within a heart in a J-shaped configuration with the bottom of the J-shape within the right ventricle and the electrode positioned at a ventricular septum or a right ventricular outflow tract such that at least a portion of the distal end of the lead body is located within a pulmonary artery.

Another aspect includes a lead body having a section of the intermediate portion of the lead body being less stiff than adjacent sections of the lead body. The lead includes an electrode coupled to the intermediate portion of the lead body and located distally from the less stiff section. The lead is adapted to be placed within a heart in a J-shaped configuration with the less stiff section near a bottom of the J-shape such that the electrode is positioned at a ventricular septum or a right ventricular outflow tract and at least a portion of the distal end of the lead body is located within a pulmonary artery. In one example, the distal end is actively fixated within the pulmonary artery.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
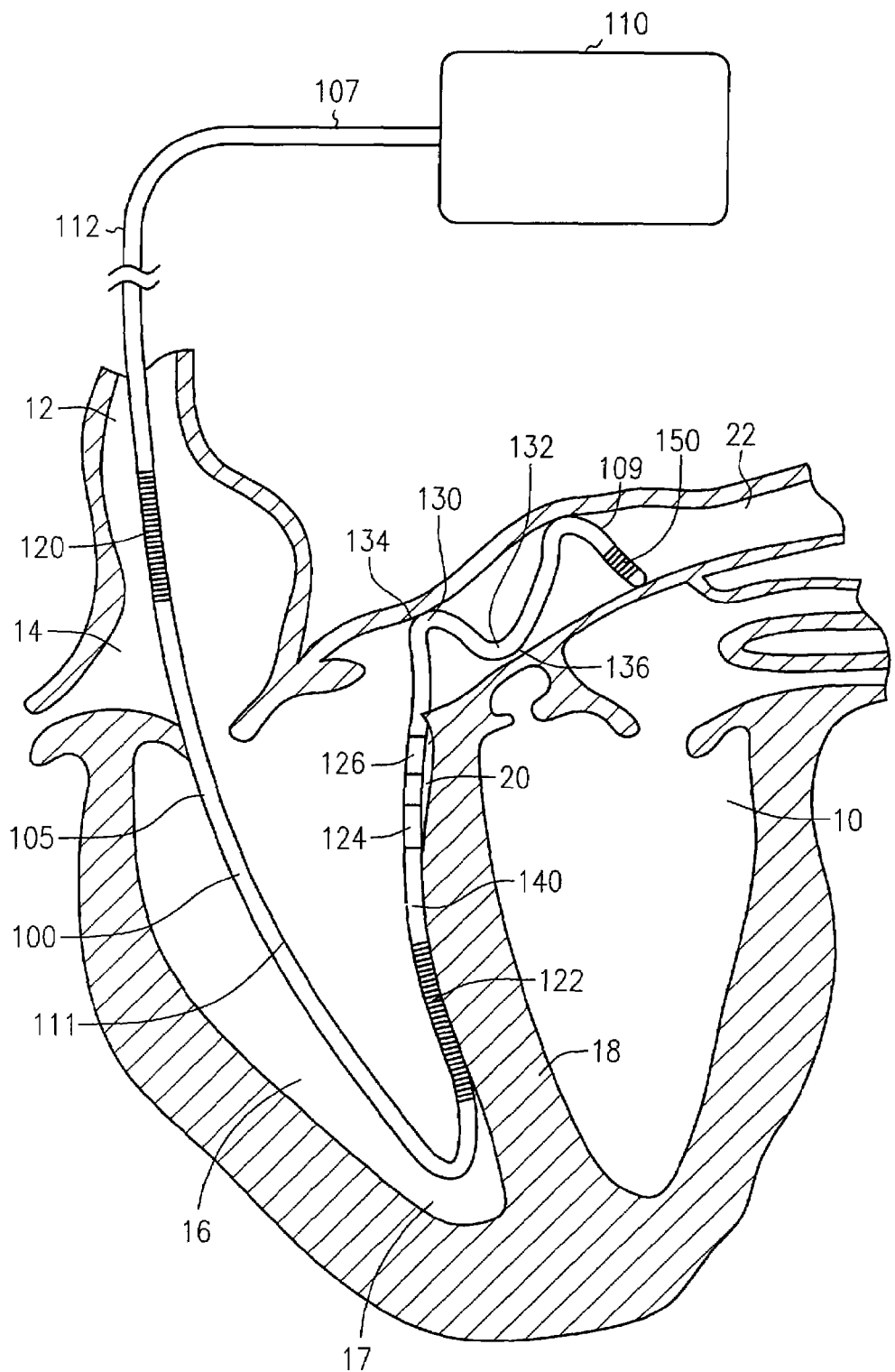
FIG. 1 shows a view of a lead, according to one embodiment, implanted within a heart.

FIG. 1 shows a view of a lead 100 implanted within a heart 10. Heart 10 generally includes a superior vena cava 12, a right atrium 14, a right ventricle 16, a right ventricular apex 17, a ventricular septum 18, and a ventricular outflow tract 20, which leads to a pulmonary artery 22. In one embodiment, lead 100 is adapted to deliver defibrillation shocks to heart 10. Lead 100 is part of an implantable system including a pulse generator 110, such as a defibrillator.

Pulse generator 110 can be implanted in a surgically-formed pocket in a patient's chest or other desired location. Pulse generator 110 generally includes electronic components to perform signal analysis, processing, and control. Pulse generator 110 can include a power supply such as a battery, a capacitor, and other components housed in a case. The device can include microprocessors to provide processing and evaluation to determine and deliver electrical shocks and pulses of different energy levels and timing for ventricular defibrillation, cardioversion, and pacing to heart 10 in response to cardiac arrhythmia including fibrillation, tachycardia, and bradycardia.

In one embodiment, lead 100 includes a lead body 105 extending from a proximal end 107 to a distal end 109 and having an intermediate portion 111. Lead 100 includes one or more conductors, such as coiled conductors or other conductors, to conduct energy from pulse generator 110 to heart 10, and also to receive signals from the heart. The lead further includes outer insulation 112 to insulate the conductor. The conductors are coupled to one or more electrodes, such as electrodes 120, 122, 124, and 126. Lead terminal pins are attached to pulse generator 110. The system can include a unipolar system with the case acting as an electrode or a bipolar system with a pulse between two of the electrodes.

In one embodiment, lead 100 is adapted for septal placement of one or more of the electrodes while utilizing pulmonary artery 22 for lead fixation. By using the pulmonary artery, the lead can be implanted such that the electrode contacts the upper portion of septum 18 above apex 17 without requiring active fixation. Lead 100 can thus shock, pace, and sense at the interventricular septum 18 or ventricular outflow tract 20.

For example, in one embodiment electrode 122 is coupled to intermediate portion 111 of the lead. Electrode 122 can be a defibrillation electrode, such as a coil defibrillation electrode designed to deliver a defibrillation shock of approximately 10 joules to approximately 50 joules to septum 18 from the pulse generator. Electrode 122 can also deliver cardioversion shocks of approximately 0.1 joules to approximately 10 joules. In one example, electrode 122 can be a spring or coil defibrillation electrode.

When present leads are inserted in the heart and positioned such that an electrode is against the high ventricular septum (above the apex 17), the leads require active fixation. However, active fixation can cause repeated trauma to the endocardial tissue because of the cyclical motion of the heart, and thus may have possible micro-dislodgement and increase defibrillation and pacing thresholds.

In one embodiment of the present system, distal end 109 of lead 100 includes a pre-formed, biased shape 130 adapted to passively fixate distal end 109 of the lead within pulmonary artery 22 with electrode 122 positioned in the right ventricle or ventricular outflow tract. In one embodiment, pre-formed, biased shape 130 includes an S-shaped configuration 132. The pre-formed, biased shape 130 generally includes at least two lead surfaces (such as surfaces 132 and 136, for example) which are dimensioned and positionable such that the surfaces contact opposing walls of the pulmonary artery.

In various embodiments, pre-formed bias shape 130 can include a curved shape such as an S-shape, a C-shape, a J-shape, an O-shape, and other non-linear shapes adapted for contacting one or more sides of the pulmonary artery to provide sufficient fixation of the lead. Such a design is more reliable because the lead becomes easier to implant and explant because of the passive fixation which is allowed by the shape of distal portion of lead 100. Moreover, passive fixation allows for easier adjustment of the electrode placement. Also, there is less trauma or perforation to endocardium tissue, which can yield lower pacing thresholds, and there is less trauma to the high septal or outflow tract than caused by active fixation at the high septal or outflow tract location. To form pre-formed biased shape 130, the lead body can be manufactured in the pre-biased shape or the conductor coil can be formed in the pre-biased shape to thus bias the lead body.

In one embodiment, electrodes 124 and 126 of lead 100 can include pacing/sensing electrodes, such as ring electrodes located distally from electrode 122. Electrodes 124 and 126 are proximal from distal end 109 and are located on the lead to sense or pace at the ventricular septum or the ventricular outflow tract when the lead is implanted.

In one embodiment, electrode 120 includes a second coil defibrillation electrode acting as a return electrode for electrode 122 in a bipolar system. Electrode 120 can be positioned in superior vena cava 12 or right atrium 14.

In one embodiment, at least a portion of lead 100 can include an anti-thrombosis coating 140, such as Hypren or polyethleneglycol for example. Coating 140 can be placed on the lead, for example on one or more of the distal electrodes 122, 124, 126, or on other segments of the lead.

In one embodiment, lead 100 can include a sensor 150, such as a cardiac output sensor, mounted proximate a distal segment of the lead or mounted on the intermediate portion of the lead. Sensor 150 is implanted to a location within the pulmonary artery or within the outflow tract 20 to monitor cardiac output through pulmonary artery 22. For example, a cardiac output monitoring sensor 150 can be placed proximate the distal end of the lead to measure cardiac output through the pulmonary artery. Sensor 150 can be coupled to pulse generator 110 through a conductor.

In one embodiment, sensor 150 can be a flow speed sensor, allowing the system to know how fast the blood is going through the artery. For example, sensor 150 can be a metal ring or coil. Such a component would have resistance properties such that if a pulse of energy was sent through the component, the component would heat up, which would in turn increase the electrical resistance of the component. The electrical resistance could be monitored over time to determine how it changes as the blood flow going past it cools it down to blood temperature. The faster the blood flow, the faster the component will cool down and hence the faster the resistance should drop. This cool down or resistance change can be correlated to the blood flow. In other embodiments, sensor 150 can be a pressure sensor. In some embodiments, sensor 150 can include a $CO_2$ or $O_2$ sensor.

In these embodiments, sensor 150 can be used to determine blood flow to allow the position of electrodes 122, 124, and 126 to be optimized. For example, the cardiac output can be used to change the position of the electrode either during or after implantation. In some examples, sensor 150 can be used to help optimize the location of other electrodes on separate leads located within the heart. Moreover, sensor 150 can be used to provide pacing and sensing information to the pulse generator to deliver pulses or modify the settings of the pulse generator.

In some embodiments, lead 100 can be configured to allow both a stylet or catheter delivery. For example, an opening can be left through the middle of the lead to allow a stylet to be used.

Figure 2:
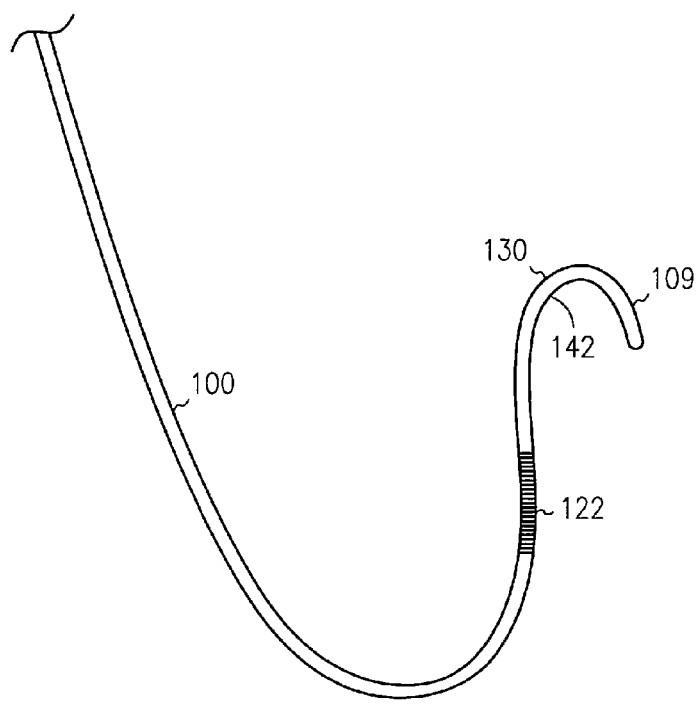
FIG. 2 shows a distal portion of a lead according to one embodiment.

FIG. 2 shows distal portion 109 of lead 100 according to one embodiment. In this example, pre-formed, biased shape 130 includes a J-shaped curve 142 at a distal tip of the lead body. J-shaped curve 142 can be positioned within pulmonary artery 22 or in one of the branch arteries off of the pulmonary artery to passively fixate the distal end of the lead within the pulmonary artery.

Figure 3:
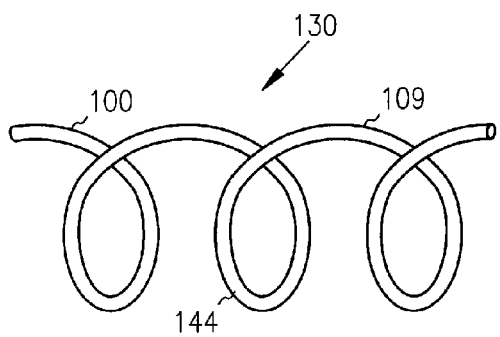
FIG. 3 shows a distal portion of a lead according to one embodiment.

FIG. 3 shows distal portion 109 of lead 100 according to one embodiment. In this example, pre-formed, biased shape 130 includes a spiral configuration 144.

Figure 4:
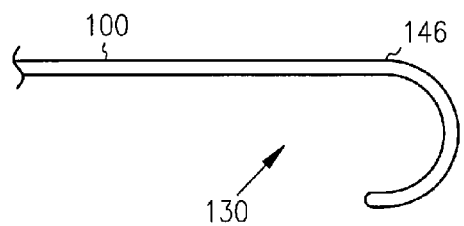
FIG. 4 shows a distal portion of a lead according to one embodiment.

FIG. 4 shows distal portion 109 of lead 100 according to one embodiment. In this example, pre-formed, biased shape 130 includes a C-shaped configuration 144.

Figure 5:
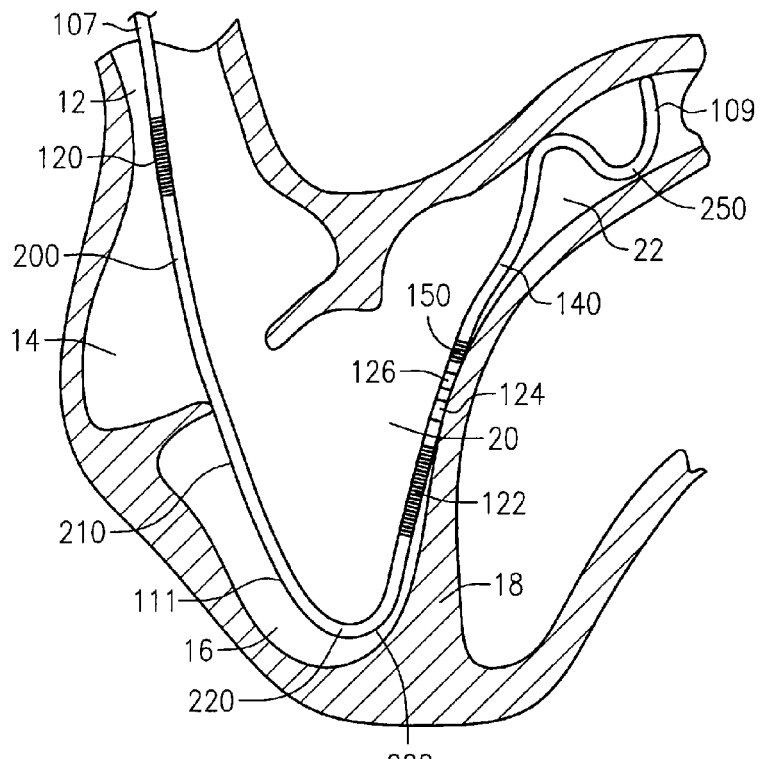
FIG. 5 shows a view of a lead, according to one embodiment, implanted within a heart.

FIG. 5 shows a view of a lead 200 according to one embodiment. Lead 200 includes some of the components discussed above for lead 100, and the above discussion is incorporated herein. Lead 200 is implanted in heart 10 with distal end 109 located within pulmonary artery 22 and electrode 122 positioned against septum 18 or within ventricular outflow tract 20.

In one embodiment, lead 200 includes a lead body 210 including a pre-formed J-shape 220 formed in the intermediate portion 111 of the lead body. J-shape 220 is located such that electrode 122 is located distally from a bottom 222 of the pre-formed J-shape 220. Various embodiments includes a pre-formed J-shape in either 2D or 3D. J-shaped portion 220 of lead 200 allows for better septal/electrode contact. To preform the lead, the lead can be manufactured such that it is biased in the J-shape. Thus, the lead naturally reverts to the J-shape when it is implanted. For example, the lead body can be formed in the pre-biased shape or the conductor coils can be formed in the pre-biased shape to bias the lead body into the shape. When implanted, the bottom 222 of the J-shape 220 is within the right ventricle 16 and electrode 122 is positioned proximate ventricular septum 18 or right ventricular outflow tract 20 such that at least a portion of the distal end 109 of the lead body is located within a pulmonary artery 22. The preformed J-lead design enhances the septal electrode stability and contact, and can help result in lower defibrillation and pacing thresholds because of better electrode contacts.

In one embodiment, a second electrode 120 is located proximally from the bottom 222 of the J-shape and positioned to be located within superior vena cava 12 or right atrium 14 when the distal end 109 of the lead is within the pulmonary artery 22. Lead 200 can also include one or more pacing/sensing electrodes 124, 126 located distally from electrode 122 to sense or pace at the ventricular septum 18 or the ventricular outflow tract 20. One embodiment includes a sensor 150, such as a cardiac output sensor. In this example, sensor 150 is located within the outflow tract 150.

In one embodiment, distal end 109 is adapted for being fixated within a pulmonary artery. One embodiment provides a passive fixation technique, as described above in FIGS. 1-4. For example, a pre-formed biased distal portion 250 can be provided. In some embodiments, to be discussed below, an active fixation technique is utilized. Some embodiments utilize neither passive nor active fixation, relying on the J-shape 220 and gravity to hold the electrodes 122, 124, and 126 in place against the septum or the outflow tract.

Figure 6:
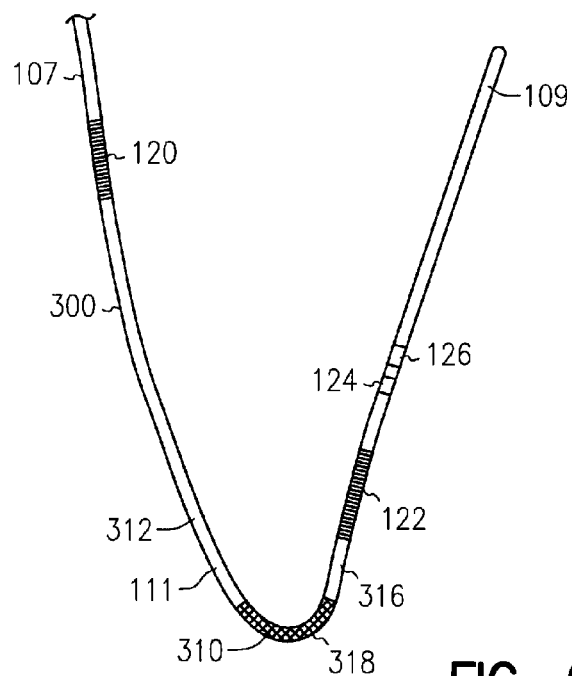
FIG. 6 shows a front view of a lead according to one embodiment.

FIG. 6 shows a front view of a lead 300 according to one embodiment. Lead 300 includes some of the components discussed above for leads 100 and 200, and the above discussion is incorporated herein. Lead 300 can be implanted in a heart (not shown) with distal end 109 located within the pulmonary artery and electrode 122 positioned against the septum or within the ventricular outflow tract.

In one embodiment, lead 300 includes a section 310 of the intermediate section 111 of the lead which is less stiff, or more pliable, than adjacent sections 312 and 316 of the lead body. Less stiff section 310 is located proximally from electrode 122 and proximally from electrode 120. When lead 300 is positioned in the heart with distal portion 109 in the pulmonary artery, the soft, or less stiff section 310 allows the lead to naturally fall into place and contact the septum due to gravity. Lead 300 is adapted to be placed within a heart in a J-shaped configuration with the less stiff section 310 near a bottom 318 of the J-shape such that electrode 122 is positioned proximate a ventricular septum or a right ventricular outflow tract and at least a portion of the distal end 109 of the lead body is located within a pulmonary artery. The less stiff section 310 helps reduce any forces caused by heart motion to be transferred to a site of the septal electrode.

In one embodiment, the less stiff section 310 includes a different, more pliable material than the material of adjacent sections 312 and 316. Again, when the lead is positioned in the heart, the softer segment allows the lead to naturally fall into place and contact the septum due to gravity, and thus enhances the septal electrode stability and contact and reduces or eliminates the forces and motion (caused by heart motion) transferred to the site of the septal electrode 122. This can result in lower defibrillation and pacing thresholds because of better electrode contact.

In this example, no fixation technique is shown in the pulmonary artery for lead 300. In other embodiments, a passive technique as shown above in FIGS. 1-5, or the active technique discussed below can be utilized.

Figure 7:
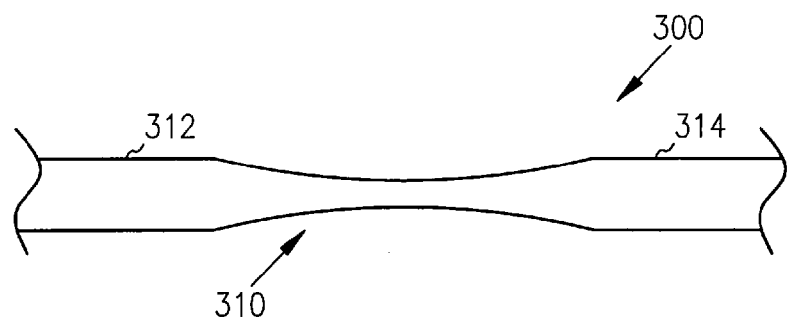
FIG. 7 shows an intermediate portion of a lead according to one embodiment.

FIG. 7 shows a portion of lead 300 according to one embodiment. In this embodiment, less stiff section 310 includes a smaller diameter than the adjacent sections 312 and 314. The smaller diameter section 310 is more flexible than the adjacent thicker regions.

In other embodiments, less stiff section 310 can be formed by providing a lead wall having a different internal diameter thickness, or by providing a less stiff conductor coil at that location.

In one example use of one or more of the leads discussed herein, the lead is inserted through the right ventricle 16 and into the pulmonary artery 22 using a guiding catheter or a stylet. The lead is positioned until the distal end of the lead is in the pulmonary artery and electrodes 122, 124, and 126 are positioned against the septum or within the outflow tract. The distal end of the lead can be fixated within the artery by one of the techniques discussed above. The pulse generator can be used to sense the activity of the heart using electrodes 124 and 126, for example. When there is need for a cardioversion or defibrillation shock, the shock is delivered via electrode 122. As discussed, in various examples, the lead body can be configured in a pre-formed J-shape such that shock electrode is located distally from a bottom of the J-shape, or a less stiff section can be provided.

Figure 8:
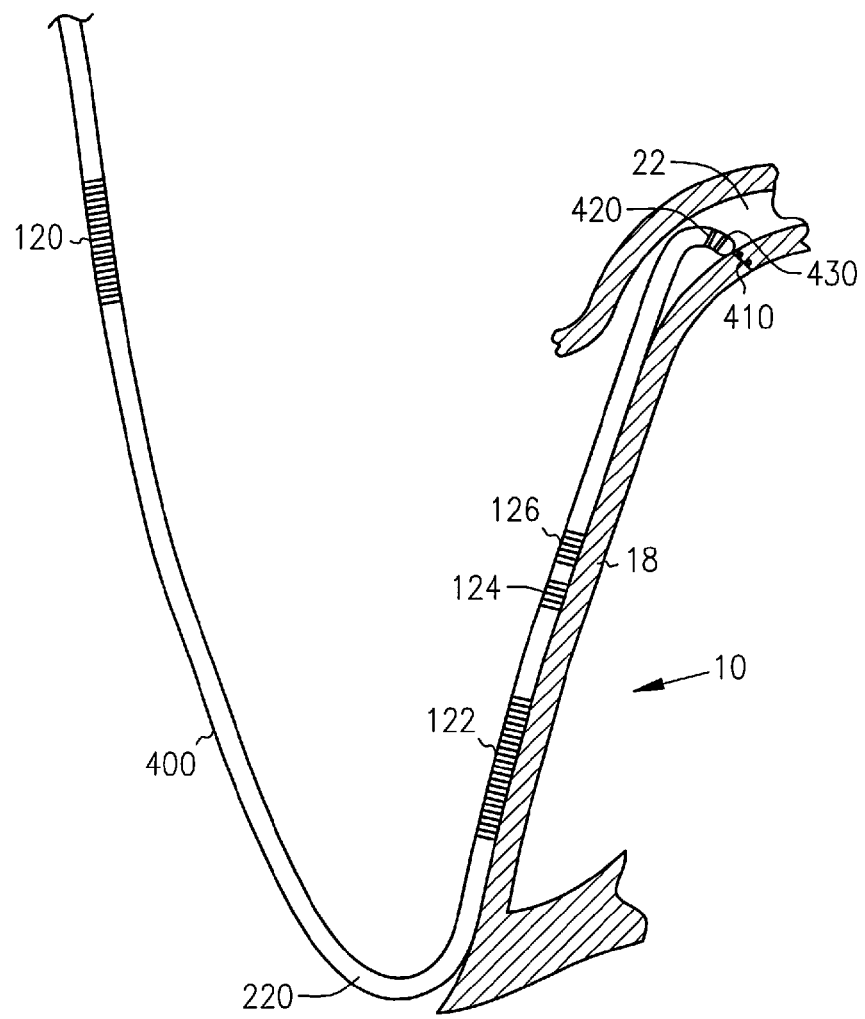
FIG. 8 shows a view of a lead, according to one embodiment, implanted within a heart.

FIG. 8 shows a view of a lead 400 according to one embodiment, implanted within a heart 10. Lead 400 is adapted to be actively fixated within the pulmonary artery 22 utilizing a helix 410, or other fixation mechanism. In one embodiment, lead 400 includes radiopaque markers 420 near the distal tip to help a physician guide the lead when viewed under fluoroscopy. One embodiment includes a drug elution member 430, which can elude steroids, for example, to reduce inflammatory response of the tissue. In some embodiments, lead 400 does not include either the pre-formed J-shape 220 (FIG. 5) or the less stiff section 310 (FIG. 6) of the leads discussed above. Lead 400 can be an unbiased, flexible lead relying on helix 410 for fixation within the pulmonary artery. In other embodiments, the active fixation technique can be used with the leads discussed above. In some embodiments, active fixation can be provided in addition to or in place of the passive fixation design discussed above.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:
providing a lead having a lead body extending from a proximal end to a distal end and having an intermediate portion, the lead having an electrode coupled to the intermediate portion, wherein the distal end of the lead includes a pre-formed, biased shape including a spiral configuration that is configured to passively fixate the pre-formed biased shape of the distal end of the lead within a pulmonary artery; and
inserting the lead through a right ventricle and into a pulmonary artery using a guiding catheter or stylet and then removing the guiding catheter or stylet when the pre-formed biased shape is in the pulmonary artery such that the electrode is proximate a ventricular septum or a ventricular outflow tract and the pre-formed biased shape of the distal end is passively fixated within the pulmonary artery.

2. The method of claim 1 further comprising delivering defibrillation or cardioversion shocks from the electrode.

3. The method of claim 1, further comprising providing a pacing/sensing electrode on the lead distally located from the first electrode.

4. The method of claim 1, wherein the pre-formed, biased shape includes at least two surfaces positioned to contact opposing walls of the pulmonary artery when the lead is implanted.

5. The method of claim 1, wherein the pre-formed, biased shape includes at least one curve in the lead body dimensioned such that at least two lead surfaces on the distal end of the lead contact at least two walls of the pulmonary artery when the lead is implanted.

6. The method of claim 1, wherein the lead body further includes a pre-formed J-shape, wherein the electrode is located distally from a bottom of the pre-formed J-shape.

7. The method of claim 1, wherein a section of the intermediate portion of the lead body is less stiff than adjacent sections of the lead body, the less stiff section located proximally from the electrode.

8. A method comprising:
providing a lead having a lead body extending from a proximal end to a distal end and having an intermediate portion, the lead having an electrode coupled to the intermediate portion, wherein the distal end of the lead includes a pre-formed, biased shape including a spiral configuration to passively fixate the pre-formed biased shape of the distal end of the lead within a pulmonary artery; and
inserting the lead through a right ventricle and into a pulmonary artery using a guiding catheter or stylet and then removing the guiding catheter or stylet when the pre-formed biased shape is in the pulmonary artery such that the electrode is proximate a ventricular septum or a ventricular outflow tract and the pre-formed biased shape of the distal end is passively fixated within the pulmonary artery such that the spiral configuration contacts a wall of the pulmonary artery in a plurality of longitudinally spaced locations.

9. The method of claim 8 further comprising delivering defibrillation or cardioversion shocks from the electrode.

10. The method of claim 8, further comprising providing a pacing/sensing electrode on the lead distally located from the first electrode.

11. The method of claim 8, wherein the lead body further includes a pre-formed J-shape, wherein the electrode is located distally from a bottom of the pre-formed J-shape.

12. The method of claim 8, wherein a section of the intermediate portion of the lead body is less stiff than adjacent sections of the lead body, the less stiff section located proximally from the electrode.

13. A method comprising:
providing a lead having a lead body extending from a proximal end to a distal end and having an intermediate portion, the lead having an electrode coupled to the intermediate portion, wherein the distal end of the lead includes a pre-formed, biased shape including a spiral configuration to passively fixate the pre-formed biased shape of the distal end of the lead within a pulmonary artery; and
inserting the lead through a right ventricle and into a pulmonary artery using a guiding catheter or stylet and then removing the guiding catheter or stylet when the pre-formed biased shape is in the pulmonary artery such that the electrode is proximate a ventricular septum or a ventricular outflow tract and the pre-formed biased shape of the distal end is passively fixated within the pulmonary artery such that the spiral configuration contacts a wall of the pulmonary artery in a plurality of radially spaced locations.

14. The method of claim 13 further comprising delivering defibrillation or cardioversion shocks from the electrode.

15. The method of claim 13, further comprising providing a pacing/sensing electrode on the lead distally located from the first electrode.

16. The method of claim 13, wherein the lead body further includes a pre-formed J-shape, wherein the electrode is located distally from a bottom of the pre-formed J-shape.

17. The method of claim 13, wherein a section of the intermediate portion of the lead body is less stiff than adjacent sections of the lead body, the less stiff section located proximally from the electrode.

* * * * *